(12) United States Patent
Whitworth

(10) Patent No.: US 8,048,436 B1
(45) Date of Patent: Nov. 1, 2011

(54) BIODEGRADABLE TREE TAG

(76) Inventor: James Curtis Whitworth, Commerce Township, MI (US)

( * ) Notice: Subject to any disclaimer, the term of this patent is extended or adjusted under 35 U.S.C. 154(b) by 1534 days.

(21) Appl. No.: 11/424,903

(22) Filed: Jun. 19, 2006

(51) Int. Cl.
 *A01N 25/34* (2006.01)
(52) U.S. Cl. .......................................... 424/411
(58) Field of Classification Search .................. 424/411
 See application file for complete search history.

(56) References Cited

U.S. PATENT DOCUMENTS

| | | | |
|---|---|---|---|
| 4,353,183 A * | 10/1982 | Estkowski | ........................ 47/56 |
| 5,307,584 A | 5/1994 | Jarvis | |
| D382,219 S | 8/1997 | Renfrew | |
| 5,669,327 A * | 9/1997 | Beebe | ........................ 116/209 |
| 5,720,129 A | 2/1998 | Lantinberg | |
| 6,516,565 B1 * | 2/2003 | Fima | ................................ 47/74 |
| 6,681,521 B1 | 1/2004 | Holloway | |
| 6,712,286 B2 * | 3/2004 | Baxter et al. | .................... 239/36 |
| 6,857,579 B2 | 2/2005 | Harris | |

\* cited by examiner

*Primary Examiner* — Johann Richter
*Assistant Examiner* — Thor Nielsen
(74) *Attorney, Agent, or Firm* — Steve M. Clemmons

(57) ABSTRACT

A biodegradable tag having a leaf-shaped body portion and an inwardly spiraling attachment appendage. The tag including at least one seed that is disposed within a seed compartment formed in the body portion. The body portion is formed from a liquid-absorbing material that absorbs a scented animal attractant liquid.

15 Claims, 2 Drawing Sheets

BIODEGRADABLE TREE TAG

FIELD OF THE INVENTION

The present invention relates to tags applied to trees and brush by hunters and outdoorsmen and more particularly, to tags that are biodegradable and receive and subsequently disperse a scented liquid.

BACKGROUND OF THE INVENTION

It is well known that game animals, such as deer, have an acute sense of smell and that it is possible to attract such animals using various scents. Currently, there are many devices used by hunters and other outdoorsmen that are used to transmit such a scent in a desired location, such as a wooded area or forest.

Most of these devices are plastic tags or applicators that are attached to tree branches at the hunting spot. These tags are either impregnated with the scent or include a fibrous pad that has the scent applied to it. While these devices are effective in transmitting the scent into the hunting area, they are oftentimes not retrieved by the hunter and are left attached to the tree/brush. Because the tags are made of a non-biodegradable material, such as plastic, they do not degrade and remain in the environment as litter for a long period of time.

Similar devices are often used as trail markers for hunters to follow to a prepared or pre-scouted hunting spot in the woods. The number of tags needed to effectively mark a trail that an individual can readily follow introduces many more non-biodegradable devices to the environment.

Further, these conventional devices are often hung on small tree branches by metal clips, wire or plastic ties that may restrict the growth of the tree and, at the least, introduces another non-biodegradable object into the woods. Other devices have a simple hole or hook arrangement in the device that allows the tag to be attached to limbs or branches that are small enough to accept the hole or hook.

Still further, these devices can only, at best, leave the environment as it was prior to placement of the device (if the device is retrieved after use). That is, these devices can only hurt the forest and cannot and do not provide any benefit to the area.

There is therefore a need for an improved tag that overcomes these and other drawbacks of conventional tags/markers and that may provide an ecological benefit to the area where the tag is deposited.

SUMMARY OF THE INVENTION

The present invention provides an improved tag that is biodegradable and may be readily attached to a branch of a tree or brush having various sizes and shapes. A liquid or atomized scent may be selectively applied to, and absorbed by, the tag to operate as a scent wick by dispersing the scent into the air over a period of time. The tag also includes a seed compartment formed in the body of the tag. This compartment retains one or more seeds, such as tree seeds, that may introduce additional vegetation/trees to the area where the tag is deposited.

In the preferred embodiment, the tag is formed from a fibrous biodegradable material that absorbs water and other liquids. The tag includes a body portion that contains the seed compartment. An elongated appendage projects from the body and is preferably shaped such that the appendage repeatedly curls in around itself.

The appendage may be uncurled and wrapped around objects of varying sizes and shapes, such as a tree limb, to couple the tag to the object.

The appendage is much narrower than the body and is formed from the same biodegradable material. As such, the appendage degrades much quicker than the body and will break due to degradation and other environmental factors (e.g., wind). The seeds enclosed in the body are thereby introduced to the forest floor and, if the proper conditions are present, will sprout new growth.

Further, the material that the tag is formed from absorbs and retains water, thereby providing the enclosed seeds with a source of water and giving the seeds an additional advantage toward maturation, especially during dry periods. In one embodiment of the invention, the seed compartment also includes fertilizer and/or nutrient-enriched natural materials, such as nitrogen and phosphorus, that will further bolster the potential introduction of new growth by the biodegrading tag.

BRIEF DESCRIPTION OF THE DRAWINGS

The description refers to the accompanying drawings in which like reference characters refer to like parts throughout the several views, and in which.

DETAILED DESCRIPTION OF THE INVENTION

Figure 1:
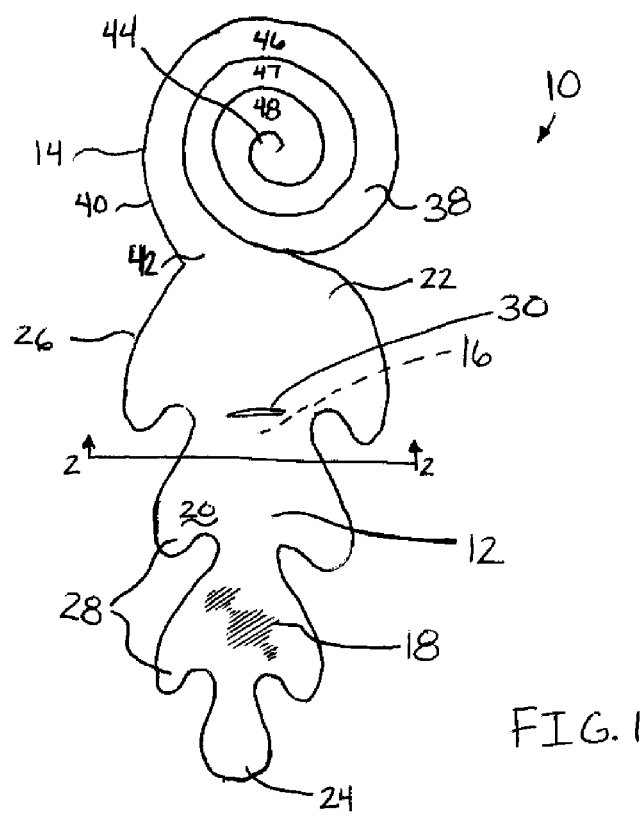
FIG. 1 illustrates a front view of a preferred embodiment of the hunter's tag.
Figure 2:
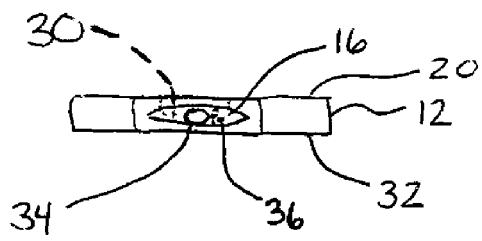
FIG. 2 is a sectional view of the hunter's tag through line 2-2.

Referring to the drawings, FIGS. 1 and 2 illustrate a preferred embodiment of tree hanger or tag 10. Tag 10 includes a body 12 and an attachment appendage 14. Body 12 includes a seed compartment 16 and includes a scented liquid 18 that is absorbed into body 12 through its outer surface.

Body 12 is a relatively thin sheet of biodegradable material that has a generally uniform thickness. In the preferred embodiment, body 12 is formed from a material that is resistant to deformation, absorbent, and lightweight, such as a fibrous biodegradable material. In one embodiment, the body is formed from a fibrous cellulose material.

Body 12 has two generally parallel outer surfaces or faces 20, 21 and has an upper portion 22 and a lower portion or tip 24. Upper portion 22 is wider than tip 24 and body 12 generally tapers down from portion 22 to tip 24.

The periphery 26 of body 12 is configured with a number of outwardly protruding lobes 28. Lobes 28 are preferably arranged along body 12 to give the body the appearance of a leaf. Additionally, the lobed shape of body 12 increases the surface area exposed to the environment (e.g., wind and rain) thereby facilitating the transfer through atomization of liquid 18 of the scent to the surrounding area and promoting the natural degradation of the biodegradable material as more material is exposed to degrading external factors.

An aperture or slit 30 is formed in surface 20. Slit 30 intersects a cavity or seed compartment 16 formed in the interior of body 12. Seed compartment 16 is disposed between the two opposing faces or surfaces 20 and 21 and may be as large as the size of the body 12 itself, depending on the amount of material desired to be placed within the compartment. That is, seed compartment 16 may be sized and shaped to follow the contours of lobes 28 while leaving only a small amount of material between the faces 20, 21 and periphery 26 and its opening.

Figure 3:
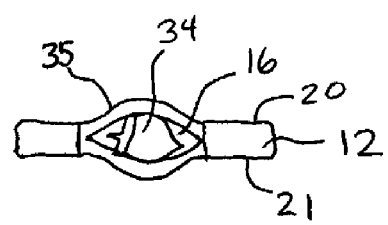
FIG. 3 is a sectional view similar to FIG. 2 illustrating a hunter's tag containing a large seed.

In one embodiment of the invention, a one or more seeds 34 are placed within seed compartment 16 via aperture 30. Seed 34 can be substantially any type of seed, but is preferably the seed of the plant represented by the shape of body 12. For example, seed 34 may be an acorn if the body 12 is shaped as an oak leaf. As shown in FIG. 3, a bulge 35 may be created in body 12 if seed 34 is larger in size than the thickness of body 12. Faces 20, 21 remain intact, however, shielding seed 34 from immediate exposure to external environmental factors.

Tag 10 may also include a plant-nutrient material 36, such as conventional plant food or fertilizer. Fertilizer 36 is disposed within seed compartment 16, surrounding seed 34 in nutrients that increase or accelerate growth. In other embodiments, body 12 may be impregnated with fertilizer 36 to slowly provide the nutrients as the body degrades around the seed.

Figure 4:
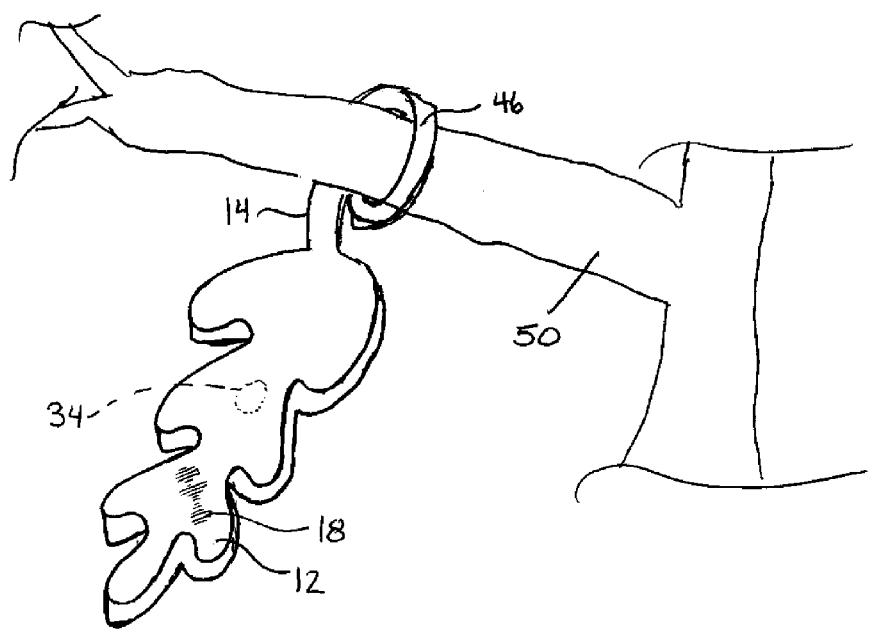
FIG. 4 illustrates a perspective view of the hunter's tag coupled to a tree branch.
Figure 5:
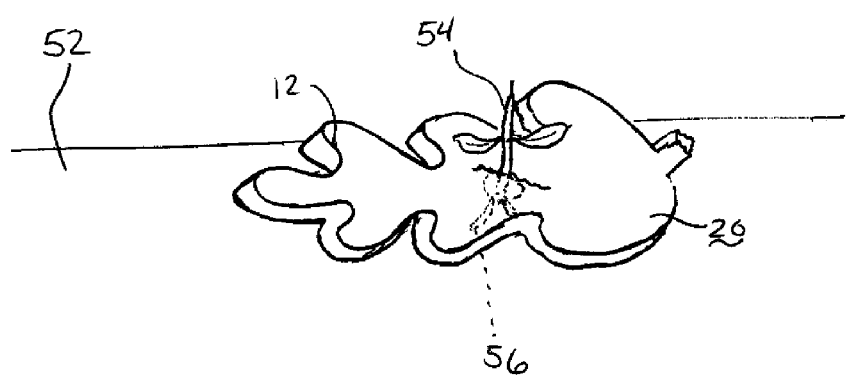
FIG. 5 illustrates the hunter's tag after falling free from the tree branch, the seed contained within the tag having sprouted into a sapling.

Referring now to FIGS. 1, 4, and 5, tag 10 also includes a coiled attachment appendage 14 that allows a user to couple or hang tag 10 to objects of various sizes and shapes. In the preferred embodiment, appendage 14 is formed from the same material as body 12 and is contiguous with the body as it projects from the edge (along periphery 26) of upper portion 22 of the body.

Appendage 14 has the same general thickness as body 12 and has upper and lower surfaces 38 and 39 that are substantially coextensive to faces 20 and 21, respectively. Appendage 14 is formed as an elongated arm or member 40 having a generally constant width that is much smaller than the width of body 12. Appendage 14 is attached at one end 42 to body 12 and extends from the body while curling in around itself to a far end 44.

As best shown in FIG. 1, coiled appendage 14 is molded or pre-formed having a generally circular shape when it is not coupled to an object. In this uncoupled state, appendage 14 has a number of spiraling rings 46-48 that, as the appendage curls in on itself, have an outer wall that abuts the inner wall of the adjacent radially outer-most ring. For example, the outer wall of ring 47 abuts the inner wall of ring 46. In the preferred embodiment, appendage 14 is a circular shaped projection extending from upper portion 22 that is spirally cut to form rings 46-48. It should be appreciated that the number of spiral rings may be changed and the three rings 46-48 illustrated are for exemplary purposes only.

Alternatively, attachment appendage 14 may be supplemented by or replaced with conventional attachment means; such as an aperture formed in body 12 or having body 12 include a hook-shaped projection extending out to couple tag 10 to various objects.

In operation, a user desiring to couple tag 10 to an object, such as tree branch 50, would uncoil attachment appendage 14 and wrap at least one of the coils, such as coil 46, around the branch 50. The pre-formed coiled shape of appendage 14 causes the appendage to grasp and hold onto the branch 50, thereby coupling tag 10 to the branch.

Because elongated member 40, which forms appendage 14, has a width that is smaller than the rest of tag 10, the appendage will degrade more quickly than the rest of tag 10. Additionally, the stress imparted on appendage 14 by other external factors, such as the wind blowing on body 12, causes biodegradable appendage 14 to break over a period of time. Preferably, appendage 14 degrades at a rate such that it will break after several months exposure to the environment.

As shown in FIG. 5, after appendage 14 has been broken, the body 12 will fall to the ground 52. Body 12 will continue to degrade over time and, if growing conditions are favorable at the location body 12 is deposited, seed 34 will sprout and potentially take root. The new growth 54 will break through the biodegrading upper-most surface (e.g., face 20), while the growth's roots 56 will pass through the opposite ground-facing surface. It should be appreciated that the addition of fertilizer 36 and the water retaining property of body 12 support the likelihood of seed 34 germinating and growing into a new tree (or other plant life). Even if seed 34 does not eventually become new growth, then, at the least, biodegradable tag 10 will gradually degrade and will not litter the woods or forest floor.

It should be appreciated that a user can use tag 10 as a conventional hunter's scent-wick by applying scented liquid 18, such as a game animal attractant, that can be left in a desired location to draw game animals to that location. The liquid-absorbing material that body 12 and appendage 14 are formed from absorbs the scented liquid and slowly releases the scent as the liquid is atomized in the air by the wind.

Further, tag 10 may be constructed in various colors and patterns that allow the user to hide the tag by giving tag 10 a camouflaged coloration. Alternatively, tag 10 may be constructed to stand-out against a natural background by giving it a bright or fluorescent color. In other embodiments, surfaces 20 and 21 may include a light reflective material to further aid a user in finding tag 10. In this manner, a user may use brightly colored tags 10 as biodegradable trail markers to assist in guiding the user to a spot in the woods.

The invention has been described in an illustrative manner, and it is to be understood that the terminology, which has been used, is intended to be in the nature of words of description rather than of limitation. Further, many modifications and variations of the present invention are possible in light of the above teachings. It is, therefore, to be understood that within the scope of the appended claims, the invention may be practiced other than as specifically described.

Having described my invention, I claim:

1. A biodegradable tag adapted to be attached to a branch, the tag comprising:
    a generally flat body having a seed compartment, said body having a minimum width;
    a coiled attachment appendage that extends from an edge of said body, said appendage is an elongated member having a generally constant width that is smaller than said minimum body width and curls inwardly upon itself to form a plurality of spiraling rings; and
    at least one seed disposed within said seed compartment;
    wherein said appendage and said body are contiguous and are formed from the same biodegradable material.

2. A biodegradable tag as provided in claim 1 wherein said body and said appendage are a fibrous, liquid-absorbent biodegradable material.

3. A biodegradable tag as provided in claim 1 further comprising a liquid having a scent, wherein said liquid is absorbed by said body.

4. A biodegradable tag as provided in claim 1 wherein said body is shaped as a leaf.

5. In combination with a tag having a generally thin body with two opposing faces; the improvement comprising:
    a seed compartment disposed within said body between said opposing faces;
    at least one seed disposed within said seed compartment; and a coiled attachment appendage that projects from said body, said appendage having an elongated member that curls in around itself at least once.

6. The combination as provided in claim 5 wherein said body and said appendage are formed from a liquid-absorbent biodegradable material.

7. The combination as provided in claim 6 further comprising a scented liquid that is absorbed into said body.

8. The combination as provided in claim 5 further comprising fertilizer that is disposed within said seed compartment.

9. A biodegradable tag adapted to be attached to a tree branch, the tag comprising:
- a generally flat body having oppositely facing front and rear surfaces running between a wide upper end and a narrow lower end, said body having a seed compartment between said front and rear surfaces;
- at least one seed disposed within said seed compartment; and
- means for removably attaching said body to a tree branch by wrapping a portion of said attachment means around said branch, wherein said attachment means is a coiled appendage that curls in and around itself at least once from a first end that is fixed to said body.

10. A biodegradable tag as provided in claim 9 wherein said body and said attachment means are contiguous and are formed from a biodegradable material.

11. A biodegradable tag as provided in claim 10 wherein said biodegradable material is a fibrous cellulose material.

12. A biodegradable tag as provided in claim 9 wherein said body has a lobed periphery.

13. A biodegradable tag as provided in claim 9 wherein said body is shaped as a leaf.

14. A biodegradable tag as provided in claim 9 further comprising fertilizer disposed within said seed compartment.

15. A biodegradable tag as provided in claim 9 wherein said body has a minimum width, and wherein said coiled appendage has a generally constant width that is smaller than said minimum body width.

* * * * *